(12) United States Patent
Wang et al.

(10) Patent No.: US 9,814,687 B2
(45) Date of Patent: *Nov. 14, 2017

(54) TRANSDERMAL PHARMACEUTICAL COMPOSITIONS INCLUDING C-SERMS FOR LOW TESTOSTERONE LEVELS IN MEN

(71) Applicant: Professional Compounding Centers of America (PCCA), Houston, TX (US)

(72) Inventors: Tsu-I Catherine Wang, Sugar Land, TX (US); Bruce V. Biundo, Houston, TX (US)

(73) Assignee: Professional Compounding Centers of America, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/831,656

(22) Filed: Aug. 20, 2015

(65) Prior Publication Data

US 2016/0051497 A1    Feb. 25, 2016

Related U.S. Application Data

(60) Provisional application No. 62/039,806, filed on Aug. 20, 2014.

(51) Int. Cl.
| | | |
|---|---|---|
| *A61K 31/136* | (2006.01) | |
| *A61K 31/138* | (2006.01) | |
| *A61K 31/194* | (2006.01) | |
| *A61K 31/568* | (2006.01) | |
| *A61K 9/08* | (2006.01) | |
| *A61K 9/06* | (2006.01) | |
| *A61K 9/00* | (2006.01) | |
| *A61K 31/00* | (2006.01) | |

(52) U.S. Cl.
CPC .......... *A61K 31/138* (2013.01); *A61K 9/0014* (2013.01); *A61K 9/06* (2013.01); *A61K 9/08* (2013.01); *A61K 31/00* (2013.01); *A61K 31/194* (2013.01); *A61K 31/568* (2013.01)

(58) Field of Classification Search
USPC ......................................... 514/651
See application file for complete search history.

(56) References Cited

U.S. PATENT DOCUMENTS

2010/0286281 A1* 11/2010 Podolski ............. A61K 31/138
514/651

OTHER PUBLICATIONS

Ruh et al. CAS: 81: 146045, 1974.*
Bebb et al., BCMJ 53(9): 474-479, 2011.*
Da Ros et al. Int Braz J Urol, 2012, 34(4):512-8.*

\* cited by examiner

*Primary Examiner* — Rei-Tsang Shiao
(74) *Attorney, Agent, or Firm* — Gable Gotwals; David G. Woodral; Scott R. Zingerman

(57) ABSTRACT

Formulations for transdermal pharmaceutical compositions including clomiphene-like selective estrogen receptor modulators (C-SERMs) in combination with transdermal penetration enhancers are disclosed. Transdermal pharmaceutical compositions can be designed with various release rates, and are administered to increase bloodstream testosterone levels and thereby reduce symptoms of testosterone deficiency in male hypogonadism or male infertility. Transdermal pharmaceutical compositions include a range of dosage forms, such as, for example solutions, liquid sprays, lotions, emulsions, creams, pastes, and ointments, among other dosage forms that exhibit transdermal properties, and provide transdermal delivery of C-SERMs. Transdermal pharmaceutical compositions will deliver C-SERMs through the skin and directly into the patient's bloodstream, thereby providing high bioavailability of C-SERMs. The dosage regimen of the transdermal pharmaceutical compositions can be easily tailored for individual patients according to the baseline blood levels of testosterone and estradiol.

16 Claims, No Drawings

TRANSDERMAL PHARMACEUTICAL COMPOSITIONS INCLUDING C-SERMS FOR LOW TESTOSTERONE LEVELS IN MEN

CROSS-REFERENCE TO RELATED APPLICATIONS

This application claims priority of U.S. Provisional Application Ser. No. 62/039,806, filed Aug. 20, 2014, which is hereby incorporated by reference.

BACKGROUND

Field of the Disclosure

The present disclosure relates generally to pharmaceutical compositions, and more particularly, to transdermal pharmaceutical compositions including clomiphene-like selective estrogen receptor modulators (C-SERMs) for testosterone deficiency.

Background Information

Male testosterone deficiency is a syndrome associated with hormonal profile changes that negatively affect libido, sexual function, mood, behavior, lean body mass, and bone density. Further, testosterone deficiency has been shown to be related to low quality of erections, loss of libido, osteoporosis, weight gain, muscle weakness, decreased lean body mass, diabetes mellitus, and cognitive changes. The decrease in serum testosterone may be due to primary testicular failure and/or dysfunction of the hypothalamic-pituitary axis. This testosterone deficiency in aging males is associated with increased body weight and adipose tissue, and changes in estrogen levels due to peripheral conversion of testosterone to estradiol. The negative feedback mechanism from excess estradiol results in a paradoxically low luteinizing hormone (LH) secretion from the pituitary gland despite a physiologically low testosterone level. Unfortunately, low LH secretion results in a decrease in testosterone production.

Currently, the most common treatment for symptomatic male testosterone deficiency is testosterone replacement therapy employing various oral and injectable delivery methods. These methods typically involve high doses of testosterone. The main purpose of the testosterone replacement therapy is to achieve normal range of testosterone serum levels.

Current oral therapy of testosterone lacks effectiveness because testosterone is metabolized extensively during the first passage of the liver before reaching the systemic blood circulation (e.g., the first-pass effect). Intramuscular injections of testosterone are widely used, but severe drawbacks for this form of treatment include local pain, soreness, minor swelling, and the unphysiologically high levels of testosterone in the body during the first days/weeks after injection. Local pain is attributed to the large volumes of testosterone injected at a specific injection site. Other drawbacks of intramuscular injections include the need for required assistance of health care professionals thereby making injections inconvenient and expensive.

Additionally, testosterone replacement therapy can be associated with side effects, such as gynecomastia, nipple tenderness, and the like. Further, long term testosterone replacement therapy will cause testicular atrophy and decline in sperm counts due to suppression of the hypothalamic-pituitary-gonadal axis via a negative feedback mechanism. Low levels of gonadotropin releasing hormone (GnRH) further decrease production of LH and follicle stimulating hormone (FSH) by the pituitary gland. The low LH levels translate to low testosterone production by the Leydig cells in the testes. The reduction in FSH could result in suppression of spermatogenesis. Physiologic inhibition of pituitary gonadotropin secretion in men by testosterone is mainly mediated by aromatization to estrogen, which inhibits hypothalamic secretion of GnRH. Therefore, there is a need for a testosterone replacement therapy that does not include the aforementioned side-effects.

SUMMARY

The present disclosure refers to transdermal pharmaceutical compositions that include clomiphene-like selective estrogen receptor modulators (C-SERMs) as APIs in combination with transdermal penetration enhancers. Further, these transdermal pharmaceutical compositions are proposed to increase testosterone levels in a patient's bloodstream and reduce symptoms of testosterone deficiency. In some embodiments, transdermal pharmaceutical compositions include one or more C-SERMs as APIs, penetration enhancers, vehicles, and additives, among other suitable ingredients.

In some embodiments, APIs include C-SERMs, such as clomiphene (Clomid®), analogs thereof, or any other chemical compound that acts on estrogen receptors to block the normal estrogen feedback control of the hypothalamus and subsequent negative feedback control on the pituitary gland.

In some embodiments, the C-SERM employed within transdermal pharmaceutical compositions is clomiphene. In these embodiments, clomiphene within transdermal pharmaceutical compositions is implemented as clomiphene citrate or an analog thereof. In other embodiments, clomiphene implemented within transdermal pharmaceutical compositions is zuclomiphene, enclomiphene, or a combination of these two clomiphene isomers.

In an example, the amount of clomiphene included within transdermal pharmaceutical compositions range from about 2% to about 10%; preferably from about 2% to about 5%. These percentages may refer to % weight by weight, % weight by volume, or % volume by volume.

In some embodiments, various additives are included to facilitate the preparation of suitable dosage forms. For example, additives include diluents, thickening agents, transdermal penetration enhancers, pH adjusters, preservatives, colors, stabilizing agents, antioxidants, and surfactants, among others.

In some embodiments, transdermal penetration enhancers provide more efficient penetration of API through skin. In these embodiments, the transdermal penetration enhancers may allow lower API dosage requirements.

In an example, the amount of penetration enhancers included within transdermal pharmaceutical compositions range from about 1% to about 50%; preferably from about 1% to about 20%. These percentages may refer to % weight by weight, % weight by volume, or % volume by volume.

In some embodiments, transdermal pharmaceutical compositions allow the delivery of C-SERMs directly into the patient's bloodstream bypassing the gastrointestinal tract and the hepatic metabolism. In these embodiments, transdermal pharmaceutical compositions will provide higher percentages of bioavailability of C-SERMs to the patient.

In some embodiments, transdermal pharmaceutical compositions include liquid dosage forms, such as, for example solutions, liquid sprays, lotions, and the like. In other embodiments, transdermal pharmaceutical compositions include semi-solid dosage forms, such as, for example emulsions, creams, pastes, ointments, and the like.

In some embodiments, transdermal pharmaceutical compositions are applied to any area of skin, such as, for example planter foot arch, lateral ankle, palm, upper arm, ventral forearm, dorsal forearm, back, chest, thigh, abdomen, groin, scalp, axilla, forehead, lower back, buttocks or scrotum, among others. In these embodiments, most suitable sites to apply transdermal pharmaceutical compositions are ventral forearm, upper arm, and chest. In other embodiments, transdermal pharmaceutical compositions are applied to those areas of skin that provide maximal systemic absorption due to increased cutaneous blood flow and heat.

In an example, transdermal pharmaceutical compositions are administered within a dosage range from about 5 mg/day to about 100 mg/day of clomiphene, preferably from about 25 mg/day to about 50 mg/day.

In some embodiments, transdermal dosage forms can be designed for fast release and transdermal absorption of C-SERMs. In other embodiments, transdermal dosage forms can be designed for slow release and transdermal absorption of C-SERMs over a prolonged period of time.

In some embodiments, a low dose C-SERM in any of the above identified dosage forms can result in acceptable testosterone levels in the patient. This contrasts with conventional testosterone replacement therapy that involves administering high dosages of testosterone.

Numerous other aspects, features, and benefits of the present disclosure may be made apparent from the following detailed description.

DETAILED DESCRIPTION

The present disclosure is here described in detail with reference to embodiments, which form a part here. Other embodiments may be used and/or other changes may be made without departing from the spirit or scope of the present disclosure. The illustrative embodiments described in the detailed description are not meant to be limiting of the subject matter presented here.

Definitions

As used here, the following terms have the following definitions:

"Absorption Enhancer" or, equivalently, "Penetration Enhancer" refers to a substance used to increase the rate of permeation through the skin or other body tissue of one or more substances (e.g., APIs) in a formulation.

"Active Pharmaceutical Ingredients (APIs)" refer to chemical compounds that induce one or more desired effects that are therapeutically or prophylactically effective.

"Clomiphene-like SERMs (C-SERMs)" refer to chemical compounds that act like clomiphene, as selective estrogen antagonist in the brain, specifically in the hypothalamus and pituitary sites. As such, the C-SERMs act to increase the release of GnRH, LH, and FSH. LH and FSH then act on the testes to increase the production of testosterone and sperm, respectively.

"Permeation enhancement" refers to an increase in the permeability of a selected active pharmaceutical ingredient (API) through the skin.

"Selective Estrogen Receptor Modulators (SERMs)" refer to chemical compounds that interact with intracellular estrogen receptors in target organs.

"Transdermal drug delivery" refers to administration of a drug to the skin surface of an individual so that the drug passes through the skin tissue and into the individual's bloodstream, thereby providing a systemic effect.

"Treating" and "Treatment" refer to reduction in severity and/or frequency of symptoms, elimination of symptoms and/or underlying cause, prevention of the occurrence of symptoms and/or their underlying cause, and improvement or remediation of damage.

"Vehicle" refers to a substance of no therapeutic value that is used to convey at least one API for administration.

Description of the Disclosure

Embodiments of the present disclosure are directed towards transdermal delivery of active pharmaceutical ingredient (APIs). Transdermal pharmaceutical compositions that include one or more clomiphene-like selective estrogen receptor modulators (C-SERMs) as APIs are disclosed. Further, these transdermal pharmaceutical compositions are proposed to increase testosterone levels in a patient's bloodstream and reduce symptoms of testosterone deficiency.

Transdermal drug delivery is receiving increased attention because it can provide a controlled release rate of active pharmaceutical ingredients (APIs) into the systemic circulation of the patient. The delivery of APIs through the skin provides many benefits. Primarily, such means of delivery is a comfortable, convenient and non-invasive way of administering APIs. The first-pass metabolism associated with oral administration is avoided, and other inherent inconveniences, such as gastrointestinal irritations, are eliminated as well.

Transdermal delivery is a particularly advantageous delivery route. It is a non-invasive drug delivery method with the benefits of better patient compliance, less risk of infection, and lower cost than invasive procedures, such as injection and implantation. Transdermal delivery may also provide a much shorter onset time (e.g., the time from administration to therapeutic effect) than oral delivery does. Transdermal applications of APIs are simple and can be administered by a caregiver or the patient with minimal discomfort.

Selective Estrogen Receptor Modulators (SERMs) are structurally unique compounds that interact with intracellular estrogen receptors in target organs. SERMs can possess either antagonist or agonist properties, and in certain cases, may possess both properties. Some SERMs, such as tamoxifen and raloxifene possess estrogen agonist properties that cause unusual pharmacological effects to be exhibited when these particular SERMs interact with certain tissues (e.g., bone, liver and cardiovascular system tissues). Additionally, these same SERMs possess estrogen antagonist properties when these particular SERMs interact with other tissues (e.g., brain and breast tissues). Finally, these same SERMs possess mixed agonist/antagonist properties when interacting with uterine tissue. Clomiphene and SERMs that mimic clomiphene act specifically as an estrogen antagonist in the brain, specifically in the hypothalamus and pituitary sites.

Testosterone is peripherally converted to estradiol that serves as a major mediator of sex steroid-gonadotropin feedback. Thus, the secretion of LH and FSH are, to a large extent, modified by C-SERMs that affect the activity of estradiol. C-SERMs possess the capacity to blunt the activity of estradiol by competing with estradiol for the estrogen receptors of the hypothalamus and pituitary gland thereby increasing the secretion of LH and FSH. These increased levels of LH and FSH correspond with increased production of testosterone and sperm, respectively. Additionally, C-SERMs may not shrink the testes thereby preserving male fertility. Therefore, C-SERMs can be indicated for both hypogonadism and male infertility.

Formulation

In some embodiments, transdermal pharmaceutical compositions include one or more C-SERMs as APIs, transdermal penetration enhancers, vehicles, and additives, among other suitable ingredients. In these embodiments, APIs include C-SERMs, such as clomiphene (Clomid®), analogs thereof, or any other chemical compound that acts on estrogen receptors to block the normal estrogen feedback control of the hypothalamus and subsequent negative feedback control of the pituitary gland.

In some embodiments, the C-SERM employed within transdermal pharmaceutical compositions is clomiphene. In these embodiments, clomiphene within transdermal pharmaceutical compositions is implemented as clomiphene citrate or an analog thereof. In other embodiments, clomiphene implemented within transdermal pharmaceutical compositions is zuclomiphene, enclomiphene, or a combination of these two clomiphene isomers.

In an example, the amount of clomiphene included within transdermal pharmaceutical compositions range from about 2% to about 10%; preferably from about 2% to about 5%. These percentages may refer to % weight by weight, % weight by volume, or % volume by volume.

In some embodiments, various additives are included to facilitate the preparation of suitable dosage forms. For example, additives include diluents, thickening agents, transdermal penetration enhancers, pH adjusters, preservatives, colors, stabilizing agents, antioxidants, and surfactants, among others.

In some embodiments, a pH adjusting agent includes sodium bicarbonate, magnesium hydroxide, calcium carbonate, dibasic calcium phosphate, tribasic calcium phosphate, sodium bicarbonate, magnesium hydroxide, potassium hydroxide, citric acid, lactic acid, hydrochloric acid, sulfuric acid, phosphoric acid, sodium phosphate monobasic, and sodium phosphate dibasic, among others.

In some embodiments, surfactants include: polysorbates, such as, for example polysorbate 20, 40, 60, and 80, among others; sorbitan esters, such as, for example sorbitan monolaurate, and sorbitan monopalmitate, sorbitan monooleate, among others; and sodium lauryl sulfate, among other surfactants known to those skilled in the art.

In some embodiments, a stabilizing agent is used to stabilize the API for a specific dosage form. In these embodiments, the stabilizing agent used will depend on the API used as well as the other additive ingredients. Any suitable chemical substance may be used as a stabilizing agent. Stabilizing agents are known to those skilled in the art and therefore will not be discussed further herein.

In some embodiments, solvents for liquid dosage forms of transdermal pharmaceutical compositions include water, liquid polyethylene glycols of various molecular weights, ethyl oleate, medium chain triglycerides, isopropyl myristate, isopropyl palmitate, isopropyl stearate, other pharmaceutically acceptable esters of C8-C22 fatty acids and C2-C6 alcohols, mineral oil, and vegetable oils, among others.

In some embodiments, transdermal penetration enhancers provide more efficient penetration of API through skin. In these embodiments, the transdermal penetration enhancers may allow lower API dosage requirements.

In some embodiments, transdermal penetration enhancers include: physical enhancers, such as, for example iontophoresis, sonophoresis, phonophoresis, magnetophoresis, electroporation, thermophoresis, radio frequency, needleless injection, hydration of stratum corneum, and stripping of stratum corneum, among others; alcohols including alkanols and alkenols, such as, for example ethanol, 1-octanol, 1-hexanol, 1-decanol, lauryl alcohol, linolenyl alcohol, and pentylene glycol, among others; alkyl-N,N-disubstituted amino acetates, such as, for example dodecyl-N,N dimethylaminoacetate, and dodecyl 2-(dimethyl amino) propanoate derivatives, among others; azone analogs with different polar heads and hydrophobic chain length, such as, for example azone, 1-alkyl or 1-alkenylaza cycloalkanones, among others; ceramide analogs with different polar heads and hydrophobic chain length; cyclodextrins (form complex with APIs and increase the absorption in the presence of other transdermal penetration enhancers); essential oils, such as, for example ajuput oil, *Alpinia oxyphylla* oil, anise oil, basil oil, cardamom oil, chamomile oil, chenopodium oil, citronella oil, black cumin oil, clove oil, *Eryngium bungei* essential oil, eucalyptus oil, fennel oil, ginger oil, lilacin oil, lavender oil, menthe oils, melissa oil, myrtle oils, neem oil, niaouli oil, nutmeg oil, orange oil, peppermint oil, petit grain oil, rosemary oil, sage oil, turpentine oils, tulsi oil, thyme oil, tea tree oil, and ylang-ylang oil, among others; fatty acid esters, such as, for example cetyl lactate, butyl acetate, and isopropyl myristate, among others; fatty acids, such as, for example capric acid, caprylic acid, cis 11,14-eicosadienoic acid, oleic acid, lauric acid, linoleic acid, linolenic acid, margaric acid, myristic acid, palmitic acid, and stearic acid, among others; propylene glycol conjugates of unsaturated fatty acids; glycols, such as, for example propylene glycol, polyethylene glycol 400, and glycerols, among others; oxazolidinones, such as, for example 4-decyloxazolidine-2-one and 3-acetyl-4-decyloxazolidin-2-one, among others; pyrrolidones, such as, for example 2-pyrrolidone, N-methyl-2-pyrrolidone, and 1-lauryl-2-Pyrrolidone, among others; sulfoxides and similar compounds, such as, for example dimethylsulfoxide, dimethylacetamide, and dimethyl formamide, among others; surfactants, such as, for example sodium lauryl sulphate, sorbitan monopalmitate, sorbitan trioleate, cetyl trimethyl ammonium bromide, benzalkonium chloride, and dodecyl betaine, among others; saponins and other herbal extracts, such as, for example *Glycyrrhiza glabra*, glycyrrhizin, Asparagus *racemosus, Aloe vera, Quillaja saponaria, Acanthophyllum squarrusom, Coptis japonica* and its alkaloidal isolates (berberine, coptisine, and palmatine), and Senkyu (*Ligustici Chuanxiong* Rhizome) ether extract, among others; terpenes and terpenoids, such as, for example alphaterpinol, alpha terpineol, alpha pinene, ascaridol, alpha bisabolol, cavacrol, carvone, 1,8 cineole, p-cymene, eucalyptol, farnesol, fenchone, geraniol, limonene, limonene oxide, linalool, menthol derivatives, thiomenthol derivatives, o-ethylmenthol derivatives, menthone, neomenthol, nerolidol, pulegone, terpinen-4-ol,tetrahydrogeraniol, thymol, trans-anethole, and verbenone, among others; transcarbam 12 derivatives, such as, for example 5-(dodecyloxycarbonyl)pentylammonium-5-(dodecyloxycarbonyl) pentylcarbamate, and iminosulfurane, such as, for example N-hexyl,N-benzoyl-S,S-dimethylimino-sulfuranes, among others; capsaicin derivatives, such as, for example nonivamide; cinnamene compounds, such as, for example cinnamic acid, cinnamaldehyde and cinnamic alcohol, among others; tranexamic acid derivatives; or urea and derivatives, such as, for example urea, 1-dodecylurea, 1-dodecyl-3-methyl urea, 1-dodecyl-3-methylthiourea, and cyclic urea derivatives, among others.

In other embodiments, transdermal penetration enhancers include: lipid synthesis inhibitors, such as, for example 5-tetradecyloxy-2-furancarboxylic acid, fluvastatin, and cholesterol sulfate, among others; phospholipids, such as, for example phosphatidyl choline from egg yolk and soybean, dimyristyl phsphatidyl glycerol, dipalmityl phophatidyl glycerol, distearyl phosphatidyl glycerol, dioleyl phosphatidyl glycerol derivatives, phosphatidyl choline derivatives from soybean and egg yolk, dioleyl phosphatidyl choline, dilinoleoyl phosphatidyl choline, hydrogenated phosphatidyl choline, and phosphatidyl ethanolamine derivatives, among others; or clofibric acid derivatives, such as clofibric acid octyl amide.

In further embodiments, transdermal penetration enhancers include: 2N-nonyl-1,3-dioxolanes; N-acetyle prolinate esters, such as, for example pentyl- and octyl-N-acetyl prolinate, among others; alkyldiloxanes, such as, for example 1-alkyl-3-b-Dglucopyranosyl-1,1,3,3-tetramethyl disiloxanes, N-arginine chitosan, dodecyl-6-(dimethylamino)hexanoate, laurocapram, decenoic acid, trypsin, transcutol, tricaprylin, oleyl pyroglutamate, 1-[2-(decylthio)ethyl]anacyclopentan-2-one, ethyl (3,6-dimethyloctylthio) acetate, and 3,7-dimethyl octyl propionate, a combination thereof; or any other chemical known to a person skilled in the art that exhibits penetration enhancing effect on transdermal absorption.

In an example, the amount of penetration enhancers included within transdermal pharmaceutical compositions range from about 1% to about 50%; preferably from about 1% to about 20%. These percentages may refer to % weight by weight, % weight by volume, or % volume by volume.

Administration

In some embodiments, transdermal pharmaceutical compositions allow the delivery of C-SERMs directly into the patient's bloodstream bypassing the gastrointestinal tract and the hepatic metabolism. In these embodiments, bypassing the gastrointestinal tract and the hepatic metabolism results in a higher percentage of bioavailability of C-SERMs to the patient.

In some embodiments, transdermal pharmaceutical compositions are applied to any area of skin, such as, for example planter foot arch, lateral ankle, palm, upper arm, ventral forearm, dorsal forearm, back, chest, thigh, abdomen, groin, scalp, axilla, forehead, lower back, buttocks or scrotum, among others. In these embodiments, most suitable sites to apply transdermal pharmaceutical compositions are ventral forearm, upper arm, and chest. In other embodiments, transdermal pharmaceutical compositions are applied to those areas of skin that provide maximal systemic absorption due to increased cutaneous blood flow and heat.

In some embodiments, transdermal pharmaceutical compositions include liquid dosage forms, such as, for example solutions, liquid sprays, lotions, and the like. In other embodiments, transdermal pharmaceutical compositions include semi-solid dosage forms, such as, for example emulsions, creams, pastes, ointments, and the like.

In some embodiments, transdermal dosage forms can be designed for fast release and transdermal absorption of C-SERMs. In other embodiments, transdermal dosage forms can be designed for slow release and transdermal absorption of C-SERMs over a prolonged period of time.

In some embodiments, transdermal pharmaceutical compositions are administered in a single administration whereby a certain amount of C-SERM is administered at once. In other embodiments, transdermal pharmaceutical compositions are administered by multiple administrations in one or more sub-doses over a specified period of time.

In some embodiments, transdermal pharmaceutical compositions may be tailored for individual patients according to clinical symptoms and baseline serum concentrations of testosterone and estradiol. In these embodiments, transdermal pharmaceutical compositions may be prescribed with various concentrations of C-SERMs and suitable dosage regimens to more closely mimic the circadian rhythm and physiological pulsatile secretion of testosterone, thereby keeping the testosterone and estradiol levels within physiologic range.

In some embodiments, the dosages (e.g., daily) required depend on the type of C-SERM included within the disclosed transdermal pharmaceutical compositions. In other words, some C-SERMs are more potent than others, and hence, the dosing can vary among the various C-SERMs used.

In an example, transdermal pharmaceutical compositions are administered within a dosage range from about 5 mg/day to about 100 mg/day of clomiphene, preferably from about 25 mg/day to about 50 mg/day.

In some embodiments, a low dose C-SERM in any of the above identified dosage forms can result in acceptable testosterone levels in the patient. This contrasts with conventional testosterone replacement therapy that involves administering high dosages of testosterone.

The following examples are intended to illustrate the scope of the disclosure and are not intended to be limiting. It is to be understood that other pharmaceutical formulations known to those skilled in the art may alternatively be used.

EXAMPLES

Exemplary dosage forms of the transdermal pharmaceutical compositions are described below.

Example #1 illustrates formula for a transdermal clomiphene citrate solution. These percentages may refer to % weight by weight, % weight by volume, or % volume by volume.

| Ingredient | Composition |
| --- | --- |
| Clomiphene citrate | 2-5% |
| Penetration enhancer(s) | 1-10% |
| Other solvents (optional) | 0-30% |
| Ethanol 190 Proof USP | q.s. 100% |

Example #2 illustrates formula for a transdermal clomiphene citrate cream. These percentages may refer to % weight by weight, % weight by volume, or % volume by volume.

| Ingredient | Composition |
| --- | --- |
| Clomiphene citrate | 2-5% |
| Penetration enhancer(s) | 1-20% |
| Cream Base | q.s. 100% |

While various aspects and embodiments have been disclosed, other aspects and embodiments are contemplated. The various aspects and embodiments disclosed are for purposes of illustration and are not intended to be limiting, with the true scope and spirit being indicated by the following claims.

What is claimed is:

1. A method of treating human male testosterone deficiency comprising applying a transdermal pharmaceutical composition to skin wherein the transdermal pharmaceutical composition comprises about 1% to about 20% a clomiphene-like selective estrogen receptor modulator (C-SERM) weight by weight and about 1% to about 70% of at least one penetration enhancer;

wherein the clomiphene-like selective estrogen receptor modulator comprises about 1% to about 10% testosterone weight by weight.

2. The method of claim 1, wherein the clomiphene-like selective estrogen receptor modulator further comprises about 1% to about 10% clomiphene citrate weight by weight.

3. The method of claim 2, wherein the transdermal pharmaceutical composition delivers about 5 mg/day to about 400 mg/day of testosterone and about 5 mg/day to about 100 mg/day of clomiphene citrate.

4. The method of claim 2, wherein the transdermal pharmaceutical composition delivers about 50 mg/day to about 120 mg/day of testosterone and about 25 mg/day to about 50 mg/day of clomiphene citrate.

5. The method of claim 2, wherein the clomiphene-like selective estrogen receptor modulator comprises about 2% to about 5% clomiphene citrate weight by weight.

6. The method of claim 1, wherein the transdermal pharmaceutical composition further comprises about 1% to about 20% of at least one penetration enhancer weight by weight.

7. The method of claim 1, wherein the transdermal pharmaceutical composition is a liquid dosage form wherein the liquid dosage form is a solution, a liquid spray, or a lotion.

8. The method of claim 1, wherein the transdermal pharmaceutical composition is a semi-solid dosage form wherein the semi-solid dosage form is selected from the group consisting of an emulsion, a cream, a gel, a paste, and an ointment.

9. The method of claim 7, wherein the transdermal pharmaceutical composition is a solution comprising about 1% to about 10% clomiphene citrate weight by weight, about 1% to about 10% testosterone weight by weight, about 5% to about 20% of at least one penetration enhancer, and ethanol.

10. The method of claim 9, wherein the solution further comprises about 0.1 to about 1% weight by weight of a thickening agent.

11. The method of claim 8, wherein the transdermal pharmaceutical composition is a gel comprising about 1% to about 10% clomiphene citrate weight by weight, about 1% to about 10% testosterone weight by weight, about 1% to about 30% of at least one penetration enhancer weight by weight, about 1% to about 5% of at least one surfactant weight by weight, about 1% to about 3% of at least one gelling agent weight by weight, and water.

12. A method of treating human male testosterone deficiency, comprising: applying a transdermal pharmaceutical composition of skin of a human male;
wherein the transdermal pharmaceutical composition comprises about 2% to about 5% of clomiphene citrate weight by weight and about 5% to about 20% of at least one penetration enhancer.

13. The method of claim 12 wherein said transdermal pharmaceutical composition further includes about 1% to about 10% testosterone weight by weight.

14. The method of claim 13 wherein the transdermal pharmaceutical composition further includes about 0.1 to about 1% weight by weight of a thickening agent.

15. The method of claim 13 wherein the transdermal pharmaceutical composition is a gel and further includes about 1% to about 5% of at least one surfactant weight by weight and about 1% to about 3% of at least one gelling agent weight by weight.

16. The method of claim 13 wherein the transdermal pharmaceutical composition further includes at least one additive selected from the group consisting of diluents, thickening agents, pH adjusters, preservatives, colors, stabilizing agents, antioxidants, surfactants.

* * * * *